United States Patent [19]

Glassman

[11] Patent Number: 4,501,580
[45] Date of Patent: Feb. 26, 1985

[54] INDWELLING CATHETERS

[76] Inventor: Jacob A. Glassman, 1680 Michigan Ave., Miami Beach, Fla. 33139

[21] Appl. No.: 459,837

[22] Filed: Jan. 21, 1983

Related U.S. Application Data

[63] Continuation of Ser. No. 215,568, Dec. 12, 1980.

[51] Int. Cl.³ .............................................. A61M 25/00
[52] U.S. Cl. ...................................... 604/43; 604/102
[58] Field of Search ..................... 604/43–45, 604/96–103

[56] References Cited

U.S. PATENT DOCUMENTS

| | | | |
|---|---|---|---|
| 1,045,326 | 12/1912 | Ruflin | 604/43 |
| 2,257,369 | 9/1941 | Davis | 604/43 |
| 3,394,705 | 7/1968 | Abramson | 604/43 |
| 3,815,608 | 6/1974 | Spinosa et al. | 604/105 |
| 3,977,408 | 8/1976 | Mackew | 604/102 |
| 4,114,625 | 9/1978 | Onat | 604/96 |
| 4,211,233 | 7/1980 | Lin | 604/43 |

FOREIGN PATENT DOCUMENTS

| | | | |
|---|---|---|---|
| 2240026 | 3/1975 | France | 604/43 |
| 2248057 | 5/1975 | France | 604/43 |

Primary Examiner—Dalton L. Truluck
Attorney, Agent, or Firm—Elmer L. Zwickel

[57] ABSTRACT

Indwelling catheters provided in their insert end with an inflatable balloon, having at least one longitudinal channel, serpentine or otherwise, on it's outside surface terminating at the insert end of the catheter spaced from the inflatable balloon. The channel has a series of ports opening into a passageway in the catheter wall that terminates at the outer end of the catheter in a fluid inlet. The fluid is delivered into the passageway through said inlet and flows through the ports and into the channel so as to irrigate or medicate the urethral canal and the outside surface of the catheter.

3 Claims, 12 Drawing Figures

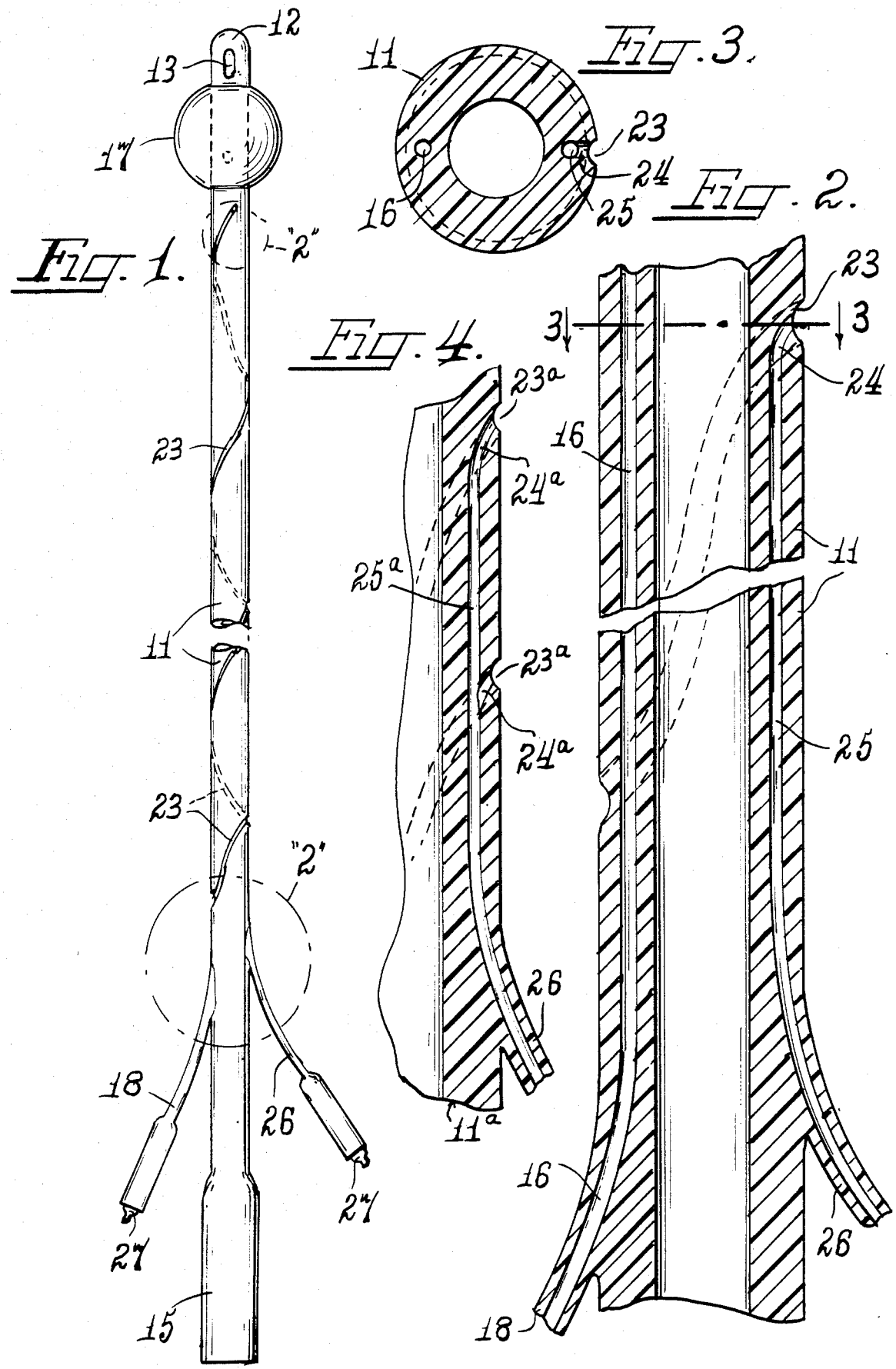

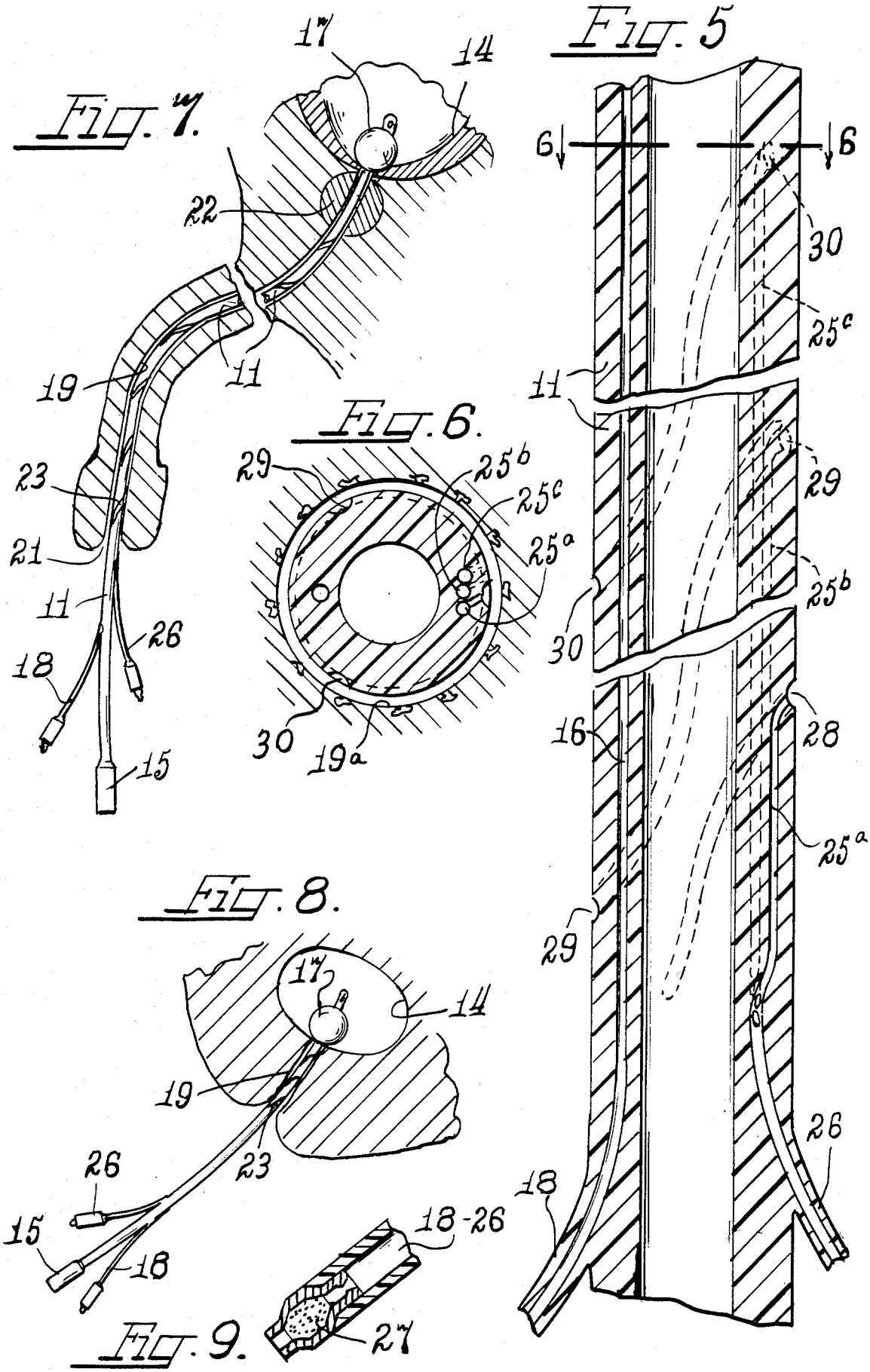

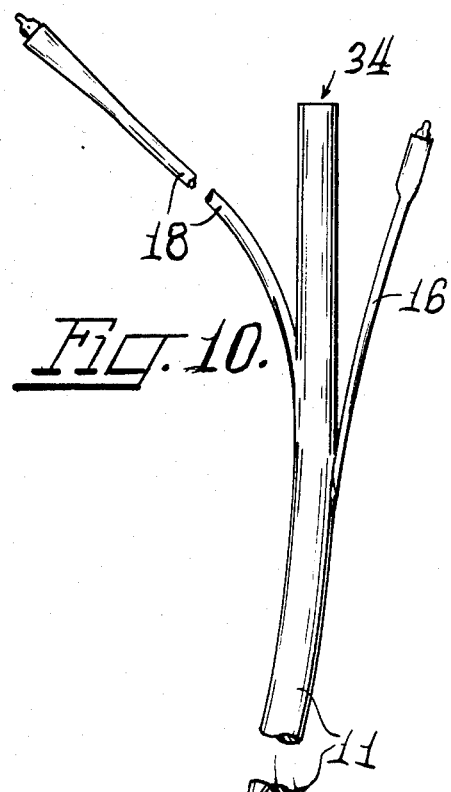
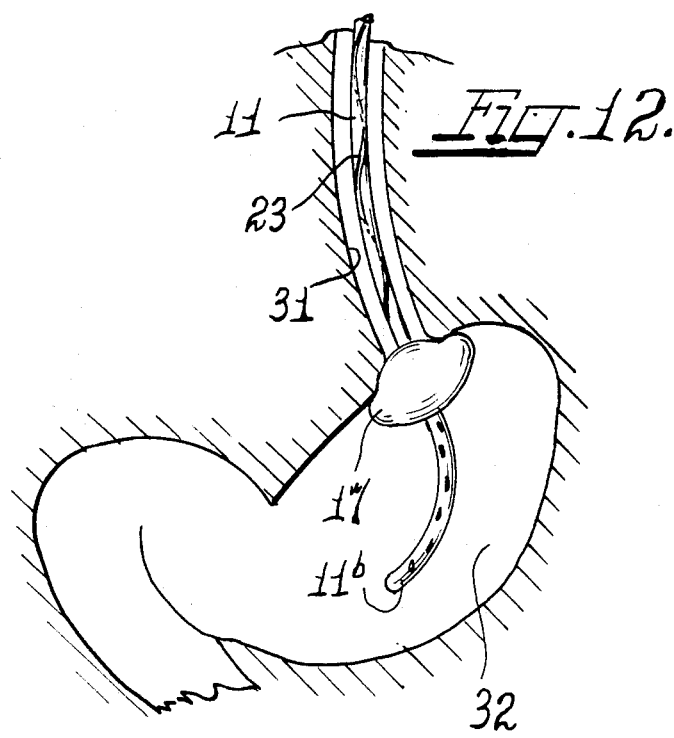
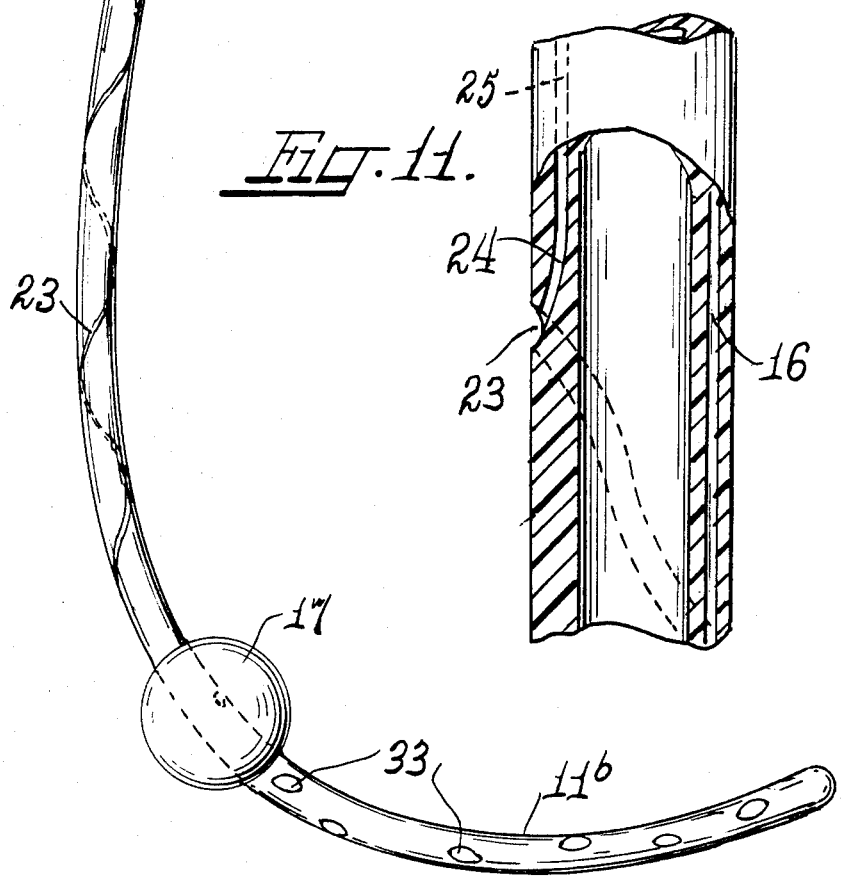

INDWELLING CATHETERS

This application is a continuation of applicant's application Ser. No. 215,568, Filed Dec. 12, 1880, in Group Art Unit 335, and formally allowed on Nov. 30, 1982, with three claims, and now abandoned. Reference is made to the prior art of record in said application.

The present invention relates to improvements in indwelling catheters (one that remains in-situ) and generally to catheters of the character show and claimed in my application Ser. No. 161,920, Filed June 13, 1980, now abandoned. The instant catheter is a balloon type catheter preferably fabricated from rubber, latex, silastic-silicon elastomer or material having similar characteristics.

Infection almost invariably follows the use of indwelling catheters in the urethra, and cystitis may spread upwardly to develop a more serious disease, i.e.: Pyleonephritis or kidney infection. It is probable that infection travels upwardly from the urethra to the bladder and then along the ureters to the kidney. The frequency of urethritis (or urethral infection) and cystitis) bladder infection) generally is about 4% or greater.

Actually, about 95% of patients with indwelling catheters develop bacteria in the urine (bacilluria) within four days, and in most instances within the first twenty-four hours; and that this could not be prevented by prophylactic use of anti-biotics. Most important were experiments by Dr. L. J. Schniederman, who collaborated with a Dr. Kass in experiments reported in an article entitled "Entry of bacteria into the Urinary Tract of Patients with inlying Catheters". published in the New England Journal of Medicine, Vol. 256; 556-7; 1957. The article demonstrated that the pathway bacteria took on the way up to the bladder was via the sheath of exudate that surrounds the catheter when within the urethra.

Another problem encountered in the use of an urethral catheter is that the urethra channel is not always sterile. Bacteria may therefore be transferred from the prostatic or/and urethral mucose into the bladder during insertion of the catheter This cannot be prevented by prophylactic use of systematic antibiotics or antiseptics instilled directly into the bladder cavity. Thus, a patient with an indwelling catheter has an open communication for bacteria between the bladder cavity and urethral canal as well as the outside of the patient's body (skin).

Another important drawback in the use of the conventional indwelling catherer is that "catheter-toilette" is not adequately carried out. Either understaffed hospital and/or inadequate nursing care may be the factors that lead to urethral catheter sepsis. However, even with the best "catheter-toilette" and even with the best urological management, an indwelling catheter left for a longer period than 45 hours may induce infection that can become most serious, and also be resistant to most forms of treatment. Since most urethral catheter caused infections originate in the glands, of the prostate gland and the urethral mucose (glands of Littre) surrounding the catheter, the best and usually the only effective means of treatments is removal of the infected catheter and treatment with appropriate anti-biotics.

Neverthe less, while it appears that good prophylactic "toilette-care" can prevent the intra-luminal path of infection, the real problem at hand still remains: The per-catheter contamination is most likely to spread upwardly. Dr. Paul B. Beeson, in an article appearing in the Yale School of Medicine publication, "American Journal of Medicine" Vol. 24, Pages 1 to 3, 1958, stated: "With regard to the indwelling catheters, where there is an open channel between the bladder cavity and the surface of the body, chemoprohylaxis could not be expected to, and indeed does not do anything but eradicate susceptible organisms and favor the establishment of an infection more difficult to treat."

The above situation relative to catheter induced infection arises also during use of catheters in the esophagus.

SUMMARY OF THE INVENTION

The improved catheter meets all of the necessary and acceptable requirements for an effective and safe indwelling catheter, the qualifications and advantages of which may be stated as follows:

1. The urinary bladder is allowed to drain effectively and the urinary flow can be accurately measured at any period of time, especially by micro-meter collectors;

2. The urinary bladder may be irrigated with sterile physiological saline, antiseptic or antibiotic solutions, without any problem. Sterile irrigation can be given separately or together, that is, a urethral canal irrigation and a bladder irrigation, or a combination of bladder, prostate, and urethral irrigation;

3. Peri-catheter obstruction and stagnation of the mucosal glandular secretions of the urethra is prevented;

4. The improved catheter eliminates the need for repeated indwelling catheterizations which so often predispose to infection, and 5. Use of the improved esophagus catheter is highly effective when in position and is further useful in sealing the esophagus opening into the stomach to prevent passage into the stomach of cleansing solutions and also to aid in the decompression of the stomach.

The various features of novelty which characterize the invention are pointed out particularly in the claims appended to and forming a part of this disclosure. For better understanding of the invention, it's operation, advantages and specific objects attained by it's use, reference should be made to the accompanying drawings and descriptive matter in which there are illustrated and described preferred embodiments of the invention.

DESCRIPTION OF THE DRAWINGS

FIG. 1 is an elevational view of one embodiment of the improved catheter, having a single flow vent and associated flow channel.

FIG. 2 is an enlarged axial sectional view of the areas of the catheter encircled in FIG. 1;

FIG. 3 is a diametrical sectional view of the catheter, taken on line 3—3 of FIG. 2;

FIG. 4 is a section of one wall of a catheter having a plurality of fluid vents and associated flow channels in communication with a single fluid inlet passage;

FIG. 5 is a sectional view similar to FIG. 2, but illustrating a plurality of fluid vents and flow channels each having it's own individual flow passage connected to a common inlet;

FIG. 6 is a diametric sectional view of the catheter, taken substantially on line 6—6 of FIG. 5, showing it in association with the inside wall of the urinary canal;

FIG. 7 is a schematic view illustrating the positioning of the indwelling catheter in the male urethra FIG. 8 is a schematic view of the indwelling urinary catheter showing it in a female urethra;

FIG. 9 is a detail sectional view of a dam contained in the open ends of the irrigation and bladder tubes;

FIG. 10 is an elevational view of a modified form of balloon catheter intended for insertion into a bleeding esophagus;

FIG. 11 is an enlarged detail axial sectional view of a channeled portion of the catheter shown in FIG. 10.

FIG. 12 is schematic view of the FIG. 10, catheter in position of use within the esophagus.

DESCRIPTION OF STRUCTURE

One embodiment of the invention is illustrated in FIGS. 1 through 3. Referring particularly to FIG. 1, the catheter comprises a tube 11 of considerable length formed of resilient material such as, for example, silicone compound or other suitable material including latex or rubber. The tube, which is basically similar to the FOLEY indwelling catheter, has a closed rounded insert end which opens into the bladder 14 as shown in FIG. 7. The outer end 15 of the tube is slightly enlarged to be telescoped over a tube (not shown) for conveying fluid (urine) from the bladder.

The wall of tube 11 includes a passage 16 opening at one end into the conventional balloon 17 adjacent tube end 12. The passage 16 is continued along the length of catheter 11 and terminates in an extension 18. When the catheter is inserted into the urethral canal 19 (FIGS. 7 and 8) and projected into the bladder 14, antiseptic fluid can be injected into extension 18 and flows through passage 16 into the balloon 17 to inflate same and cause it to set on the floor of the bladder to anchor itself in the bladder and, more important, to restrain urine leakage. Urine leaking from the bladder and running down on the outside of the catheter defeats the doctor's ability to measure drainage and often contributes to the aforesaid formations and subsequent gram-negative infection with possible systematic infection and sepsis.

In order to negate the many dangers of probable urinary drainage down along the outside of the catherer, the improved catheter embodies novel means to wash the outside surface of the catheter and the walls of the prostatic and canal wall 19a. As best shown in FIGS. 1 and 7, the length of the catheter tube 11, from about the point of entrance (21) into the urethral canal 19 to approximately the top of the prostate gland 22 (FIG. 1); or the female bladder (FIG. 8), has formed, on it's outside surface, at least one shallow channel 23. The channel may be straight, longitudinally spiral or serpentine, or it may be otherwise suitably arranged, but directed in such direction that any fluid therein will flow in the direction of the outer end of the catheter. Channel 23 has it's end closest to the balloon 17 in flow communication through a vent 24 with an axial passage 25 in the catheter wall. The passage extends from vent 24 to an external extension 26 having a penetratable block 27 (FIGS. 1 and 9) at its end to admit a sterile needle required to inject the sterile anti-septic or anti-biotic fluid into passage 25 and thence into the external channel or channels 23. The stirile fluid tends to flow the full length of the channel but in doing so it effectively spills over onto the external surface of the catheter and the mucosa of the urethra and prostatic canals. In this manner the urethral wall 19a, (Glands of Littre) as well as the prostatic canal and outside surface of the catheter 11 are effectively bathed, and any incrustation thereon is dissolved and/or physically washed away. Also, any bacteria that may have been deposited on the catheter before and/or during insertion will be eliminated by the chemical and physical action of the irrigating fluids. Hence, the probability of bladder infection (cystitis) will be minimized if not entirely prevented.

Further, the free flow of fluid along channel 23 within the confines of the prostatic gland 22 is not impeded by the swelling of an infected prostate gland which tends to bind itself snugly about the related portion of the catheter. When a catheter is devoid of a channel or channels withing the area of the prostatic urethra there will be such a tight fit around the catheter that all flow or irrigation fluids in the prostatic urethra will be prevented.

The catheter illustrated in FIG. 4 is somewhat similar to that described hereinabove and like numbers identify like parts. The only material difference in this disclosure is that the catheter tube 11a is provided with two external channels 23a, both of which communicate with a single passage 25a through vents 24a. Of course, as indicated earlier, three and perhaps 4 channels may be provided. This is illustrated in FIGS. 5 and 6. As shown, each of the channels 28, 29 and 30 is in flow communication with it's own passageway 25a, 25b and 25c, all of which merge into a common inlet passageway terminating in an extension 26 having a penetratable block 27 at it's outer end.

Irrespective of the number and configuration of the channels and the number of passageways in the catheter connecting the channels, there is a total bathing and irrigating of the outer surface of the catheter and of the wall 19a of the urethral canal 19 so as to irrigate and physically remove all bacteria and debris from the outside surface of the catheter and from the entire canal wall; i.e. (prostatic and urethral mucosal lining).

With reference to the teaching in FIGS. 10, 11 and 12, the catheter there illustrated is intended for use in the esophagus 41 or locally treating, with astringents, such as adrenalin and thrombin solutions. Such solutions are extruded through vents 35 (FIG. 10) leading from a wall passage or passages 36 in the catheter, for delivery into an external channel or channels 34. These channels effectively distribute solution over the external surface of the catheter and onto the interior surface of the esophagus wall. In order to prevent the astringents from flowing downwardly on the outside surface of the catheter end portion 11c into the stomach 42, the catheter is provided with a balloon 17 adjacent it's lower end which, when inflated as earlier described herein, will effectively press against the upper wall of the stomach and block the escape of fluids donwardly.

The catheter also is concerned with the provision of means to aid in decompressing the stomach. Here the portion of the catheter 11c projecting below balloon 17, is provided with a plurality of perforations 43 useful to decompress the stomach when suction means is attached to the exposed open end 44 of the catheter tube.

While specific embodiments of the invention have been shown and described in detail to illustrate the application of the invention, it will be understood that the invention may be embodied in other manners without departing from the principles herein desclosed.

What is claimed is:

1. A catheter for use in the irrigation of a bladder and flushing of urethral and prostatic canal, comprising;
    a. a flexible tubular member having an annular wall of uniform diameter;
    b. said wall having exterior and interior surfaces;

c. said tubular member having a closed end for insertion into the bladder and an open outer end;
d. an annular inflation balloon adjacent the insertable end of said tubular member;
e. the interior surface of said tubular member forming an axial flow duct of uniform diameter having at least one drain hole near said closed end to receive fluid drainage from the bladder;
f. a passage in the wall of said tubular member extending from said tubular outer end and opening at it's other end into the interior of said balloon;
g. a relative deep channel in said exterior surface of said tubular member extending from adjacent the open outer end of said member into close proximity with the balloon;
h. a fluid passageway in the annular wall of said member: and
i. at least one radial vent in said tubular member flow-connecting said fluid passageway with said channel whereby fluid delivered through the vent enters the channel for distribution on the walls of the prostatic and urethral canals to eliminate ascending infection in said channel.

2. A catheter comprising:
a. a flexible tubular member for insertion into the urethral and prostatic canals having an annular wall;
b. said wall having outer and inner surfaces;
c. said tubular member having an insertable end and an open outer end;
d. said inner surface of the annular wall forming an axial flow duct opening through both ends of the tubular member for draining purposes;
e. an inflatable balloon secured to the tubular member adjacent it's insertable end;
f. at least one passageway for sterile fluid in the annular wall extending from said outer end and terminating short of said insertable end;
g. at least one channel in the outer surface of the said annular wall starting from adjacent the said open end and terminating just short of the balloon; and
h. at least one flow duct connecting the passageway with the channel to admit sterile fluid from the passageway into the channel for irrigating the urethral and prostatic canals.

3. The catheter recited in claim 2, wherein the channel is serpentine in configuration and of sufficient depth to insure fluid flow therein when the prostate is swollen.

* * * * *